United States Patent
Baker et al.

(10) Patent No.: US 6,846,830 B2
(45) Date of Patent: Jan. 25, 2005

(54) NAPHTALENE DERIVATIVES AND THEIR PHARMACEUTICAL USE

(75) Inventors: Stephen Richard Baker, Yateley (GB); David Bleakman, Zionsville, IN (US); Carlos Lamas-Peteira, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/221,822

(22) PCT Filed: Mar. 19, 2001

(86) PCT No.: PCT/US01/05817

§ 371 (c)(1), (2), (4) Date: Sep. 16, 2002

(87) PCT Pub. No.: WO01/72709

PCT Pub. Date: Oct. 4, 2001

(65) Prior Publication Data

US 2003/0073725 A1 Apr. 17, 2003

(30) Foreign Application Priority Data

Mar. 29, 2000 (ES) .......................................... 00500050

(51) Int. Cl.$^7$ ...................... C07D 213/02; A61K 31/44; A61K 31/445

(52) U.S. Cl. ........................ 514/277; 514/317; 514/345; 546/1; 546/192; 546/301

(58) Field of Search ................................ 546/192, 301, 546/1; 514/317, 345, 277

(56) References Cited

PUBLICATIONS

Clark et al, European Journal of Pharmacology, vol. 27, pp. 34–39, 1974.*

Waters et al, Journal of Medicinal Chemistry, vol. 29, pp. 1512–1561, 1986.*

* cited by examiner

*Primary Examiner*—Zinna Northington Davis
(74) *Attorney, Agent, or Firm*—Arvie J. Anderson; Mark A. Winter

(57) ABSTRACT

Use of compounds of the formula (I) where A, E, $R^1$, $R^2$, p and q have the meanings given in the specification are GluR6 antagonists useful for the treatment of disorders of the central nervous system.

31 Claims, No Drawings

NAPHTALENE DERIVATIVES AND THEIR PHARMACEUTICAL USE

This application is a U.S. national phase entry, prudent to 35 USC 371, of PCT/US01/05817, filed Mar. 19, 2001 and published on Oct. 4, 2001, International Publication No. WO 01/72709 A1, which claims the benefit of Spanish Application No. ES 00500050.0 filed Mar. 29, 2000.

The present invention relates to certain naphthalene derivatives which are useful as pharmaceuticals. More particularly it relates to a new pharmaceutical use for novel and known naphthalene derivatives, to novel naphthalene derivatives, to a process for preparing the novel naphthalene derivatives and to a pharmaceutical composition comprising naphthalene derivatives.

L-Glutamate mediates excitatory neurotransmission in the mammalian central nervous system through its action at glutamate receptors. There are two broad classes of glutamate receptors, known as the ionotropic glutamate receptors and the metabotropic glutamate receptors. Within the class of ionotropic glutamate receptor are three classes, known as the N-methyl-D-aspartate (NMDA), (R,S)-2-amino-3-(3-hydroxy-5-methyl-isoxazol-4-yl)propanoate (AMPA) and kainate (KA) receptors. Molecular biological studies have established that AMPA receptors are composed of subunits (GluR1-4) that can assemble to form functional channels. Five kainate receptors, classified as either high affinity (KA1 and KA2) or low affinity (GluR5, GluR6 and GluR7) kainate receptors have been identified. (Bleakman et al, *Molecular Pharmacology*, 1996, Vol. 49, No. 4, pgs. 581–585 and Hollmann, M., and Heinemann, S., Cloned Glutamate Receptors, Ann. Rev. Neurosci. 1994, 17:31–108).

J. Org. Chem., Fozard and Bradsher, vol. 31, pag. 3683–5 describes the synthesis of 2-[2-(2-(1-chloro)naphthyl)vinyl]pyridine.

J. Organometallic Chem., 108, (1976), 175–181 describes the synthesis of 2-[2-(2-(1-bromo)naphthyl)vinyl]pyridine.

JCS Perkins II, 1975, 1712-5 discloses unsubstituted naphthylvinylpyridine analogues.

J. Med. Chem., 1971, vol. 14, 315–22 discloses 4-[2-(2-naphthyl)vinyl]pyridine useful in the inhibition of brain choline transferase.

J. Med. Chem., 1972, vol. 15, 1168–71 discloses 4-[2-(2-naphthyl)vinyl]-2-nitropyridine which possess an anthelmintic effect.

J. Med. Chem., 1969, vol. 12, 134–38 discloses 4-[2-(2-naphthyl)vinyl]pyridine and 4-[2-(2-naphthyl)acetinyl]pyridine useful as choline acetyltransferase inhibitors.

J.O.C., vol. 49, 1984, 2546–51 discloses 4-[2-(2-(6-dialkylamino)naphthyl)vinyl]pyridine derivatives useful as intermediates for the synthesis of charge-shift probes of membrane potential.

J. Med Chem.,1993, vol 36, 1278–83 discloses 4-[2-(2-naphthyl)vinyl]pyridine and 4-[2-(2-naphthyl)ethyl]pyridine useful as substrates of Monooxidase A &B.

Accordingly, the present invention provides the use of a compound of general formula:

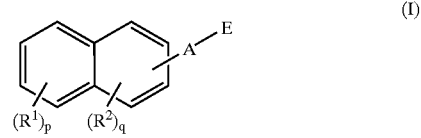

(I)

where p is 0 to 4, q is 0 to 3,
—A— represents a group —CHR$^3$—CHR$^4$—, —CR$^5$=CR$^6$—, —C≡C, or —COO—,
wherein R$^3$ is hydrogen or hydroxy,
R$^4$, R$^5$ and R$^6$ are each independently hydrogen or C$_1$–C$_6$ alkyl, a substituted or unsubstituted phenyl, carboxy(C$_1$–C$_6$) alkyl or cyano;
—E represents a substituted or unsubstituted heterocycle;
R$^1$ and R$^2$ are each independently selected from C$_1$–C$_6$ alkyl, hydroxy, C$_1$–C$_6$ alkoxy, nitro, cyano, C$_1$–C$_6$ alkylthio, halogen, trifluoromethyl, a substituted or unsubstituted phenyl, a substituted or unsubstituted benzyl or a group represented by —O—(CH$_2$)$_{m'}$—Y, in which Y represents C$_3$–C$_6$ cycloalkyl, C$_2$–C$_6$ alkenyl, C$_2$–C$_6$ alkynyl, a substituted or unsubstituted phenyl, C$_1$–C$_6$ alkoxy, and m' is 0 or 1;
or a pharmaceutically acceptable salt or ester thereof,
provided that when m' represents 0, Y represents C$_3$–C$_6$ cycloalkyl or a substituted or unsubstituted phenyl; for the manufacture of a medicament for the treatment of a condition indicating treatment with a GluR6 antagonist.

The present invention also provides a method of antagonising the action of L-glutamate at GluR6 receptors in a warm blooded mammal requiring such treatment, which comprises administering to said mammal an effective amount of a compound of general formula I, or a pharmaceutically acceptable salt thereof as defined hereinabove.

As described hereinabove, compounds of formula I have been found to be antagonists of L-glutamate at GluR6 receptors. They have further been found to be non-competitive antagonists. In other words, their antagonist effect has been found to be unaffected by increasing concentration of agonist. Furthermore, it has been found that their action is both use-dependent and voltage-dependent. This term relates to compound activity at ion channels where compound activity appears dependent upon ion channel opening and/or ion influx through the channel. Thus the ability of the compound to block the channel is enabled by the opening of the channel. Likewise, reversal of the compound inhibition is enabled by repeat application of agonist (glutamate). These are features compounds that act as 'use-dependent molecules' such that the accumulation of inhibition with repetitive stimuli has beed termed use-dependence (Courtney, K. R., J. Pharm. Expt. Ther. 195, 225–236, 1975). In particular, it has been found that the compounds exhibit a slow onset of inhibition which develops with agonist-dependent ion channel activation and reverses at a rate dependent upon agonist-dependent activation. Inhibition has also been observed at hyperpolarised (negative) membrane potentials during ion influx, but not at depolarised (positive) potentials during ion efflux under whoile cell voltage clamp recording conditions. Use-dependence molecules may have therapeutic advantage inasmuch that compound activity may (i) be preferentially restricted to neurons that are excited by glutamate actions at GluR6 in particular CNS disorders and/or (ii) have a duration of action enhanced (longer biological half life) were reversal of inhibition dependent upon ion channel opening.

A variety of physiological functions have been shown to be subject to influence by excessive or inappropriate stimulation of excitatory amino acid transmission. The formula I compounds of the present invention are believed, through their action as GluR6 antagonists, to have the ability to treat a variety of neurological disorders in mammals associated with this condition, including acute neurological disorders such as cerebral deficits subsequent to cardiac bypass surgery and grafting, stroke, cerebral ischemia, spinal cord lesions due to trauma or infarction/ischaemia or inflammation, head trauma, perinatal hypoxia, cardiac arrest, and hypoglycemic neuronal damage, and chronic neurological disorders, such as Alzheimer's disease, Huntington's Chorea, inherited ataxias, amyotrophic lateral sclerosis, AIDS-induced dementia, ocular damage and retinopathy, cognitive disorders, Parkinson's Disease, drug-induced Parkinsonism and essential tremor. The present invention also provides methods for treating these disorders which comprises administering to a patient in need thereof an effective amount of a compound of formula I, or a pharmaceutically acceptable salt thereof.

The formula I compounds of the present invention are also believed, through their action as GluR6 antagonists, to have the ability to treat a variety of other neurological disorders in mammals that are associated with glutamate dysfunction, including muscular spasms, convulsions (such as epilepsy), spasticity, migraine headache, cluster headache, chronic daily headache, urinary incontinence, psychosis, (such as schizophrenia or bipolar disorder), post traumatic stress disorder, depression, drug tolerance and withdrawal (such as alcohol, nicotine, opiates and benzodiazepines), drug intoxication, metabolic derangement, anxiety and anxiety related disorders such as post-traumatic stress syndrome, emesis, brain edema, pain (acute and chronic, neuropathic or retractable, post traumatic pain), and tardive dyskinesia. Therefore, the present invention also provides methods for treating these disorders which comprise administering to a patient in need thereof an effective amount of the compound of formula I, or a pharmaceutically acceptable salt thereof.

The term "treating" for purposes of the present invention, includes prophylaxis, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

It will be appreciated that the compounds of formula (I) may contain one or more asymmetric carbon atoms, especially wherein $R^3$ is OH. Accordingly, the compounds of the invention may exist in and be isolated in enantiomerically pure form, in racemic form, or in a diastereoisomeric mixture. The present invention includes all such forms.

In the above general formula, the term $C_1$–$C_6$ alkyl group means a straight or branched alkyl group containing from 1 to 6 carbon atoms. It includes the terms $C_1$–$C_5$ alkyl and $C_1$–$C_4$ alkyl. Examples of particular values for a $C_1$–$C_6$ alkyl group are methyl, ethyl, propyl, isopropyl, butyl and isobutyl, and is preferably methyl or ethyl.

Examples of particular values for a $C_2$–$C_6$ alkenyl group include, vinyl, prop-2-enyl, but-3-enyl, pent-4-enyl and isopropenyl, and an alkenyl group can contain more than one double bond. A preferred alkenyl group is vinyl.

Examples of particular values for a $C_2$–$C_6$ alkynyl group include, prop-2-ynyl, but-3-ynyl and pent-4-ynyl, and is preferably of the formula R"C≡C— where R" is $C_1$–$C_4$ alkyl.

Examples of particular values for a $C_3$–$C_6$ cycloalkyl group are cyclopropyl, cyclobutyl, cyclopentyl or cyclohexyl and these groups may optionally be substituted by one or more $C_1$–$C_4$ alkyl, for example methyl, or ethyl substituents.

The terms $C_1$–$C_6$ alkoxy or a $C_1$–$C_6$ alkylthio are an alkyl group linked to an oxygen or a sulphur atom, where the alkyl is as defined above. Examples of particular values for a $C_1$–$C_6$ alkoxy or a $C_1$–$C_6$ alkylthio group include methoxy, ethoxy, thiomethyl or thioethyl.

Examples of particular values for halogen include fluoro, chloro and bromo, preferably fluoro or chloro.

The term $C_1$–$C_6$ acylamino means a $C_1$–$C_6$ alkyl group linked to an amide group, where the $C_1$–$C_6$ alkyl is as defined above. It includes a group of the formula $R^{IV}$—NH—CO— where $R_{IV}$ is $C_1$–$C_5$ alkyl. An Example of a particular value of a $C_1$–$C_6$ acylamino group includes acetamide.

In the above general formula, a substituted phenyl, benzyl or phenoxy group is substituted by one or more, for example from one to three substituents, selected from $C_1$–$C_6$ alkyl, especially methyl, $C_1$–$C_6$ alkoxy, especially methoxy and ethoxy, carboxy, hydroxy, cyano, halogen, especially bromo, chloro and fluoro, trifluoromethyl, nitro, amino, $C_1$–$C_6$ acylamino, $C_1$–$C_6$ alkylthio, a unsubstituted or phenyl substituted by one to three substituents selected from $C_1$–$C_6$ alkyl, $C_1$–$C_6$ alkoxy, trifluoromethyl or halogen, and a unsubstituted or phenoxy substituted by one to three substituents selected from $C_1$–$C_6$ alkyl, $C_1$–$C_6$ alkoxy, trifluoromethyl or halogen.

A substituted heterocycle includes a five, six or seven membered ring containing one or more heteroatoms selected from N, O or S, and can be saturated or unsaturated. When a heterocycle contains a nitrogen atom, it can be linked to a carbon atom in the ring and it can also be linked through the nitrogen atom. Examples of particular values for heterocyle include compounds of the formula:

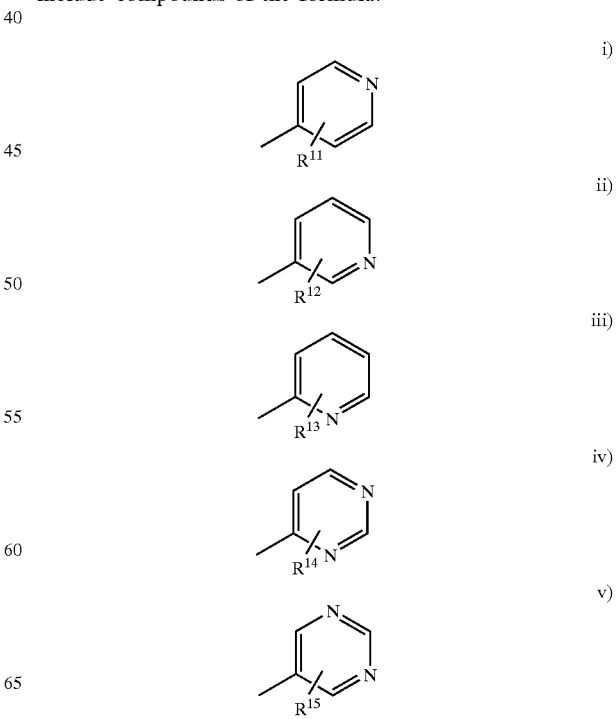

-continued vi)
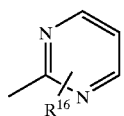

vii)
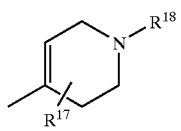

viii)
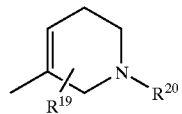

ix)
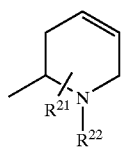

x)
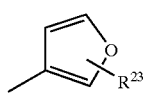

xi)
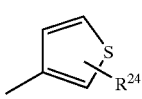

xii)
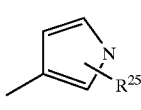

xiii)
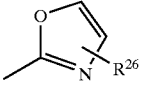

xiv)
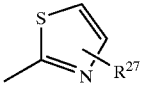

xv)
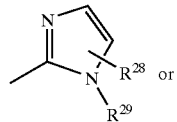 or xvi)
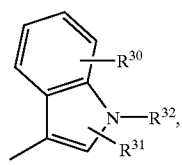

wherein $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ are each independently selected from $C_1$–$C_6$ alkyl, especially methyl, $C_1$–$C_6$ alkoxy, especially methoxy and ethoxy, carboxy, hydroxy, cyano, halogen, especially bromo, chloro and fluoro, trifluoromethyl, nitro, amino, $C_1$–$C_6$ acylamino, $C_1$–$C_6$ alkylthio, a substituted or unsubstituted phenyl, a substituted or unsubstituted benzyl and a substituted or unsubstituted phenoxy.

Examples of particular values for $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ include $C_1$–$C_6$ alkyl, especially methyl, $C_1$–$C_6$ alkoxy, especially methoxy, halogen, especially chloro and fluoro, trifluoromethyl, amino, a substituted or unsubstituted phenyl, and a substituted or unsubstituted phenoxy.

In the compounds of formula I,

—A— preferably represents —CHR³—CHR⁴— or —CR⁵=CR⁶—. Most preferably —CR⁵=CR⁶—. It will be understood that when —A— is —CR⁵=CR⁶— the double bond can be cis or trans. Both isomers are part of the invention. Preferably the double bond is trans.

$R^3$ preferably represents hydrogen.

$R^4$ preferably represents hydrogen.

$R^5$ preferably represents hydrogen.

$R^6$ preferably represents hydrogen.

Accordingly, examples of particular values for —A— are —E preferably represents a heterocycle selected from:

i)
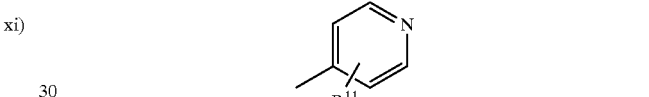

ii)
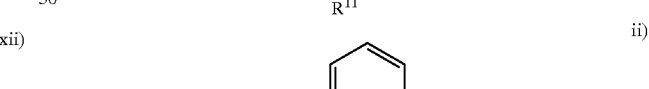

iii)
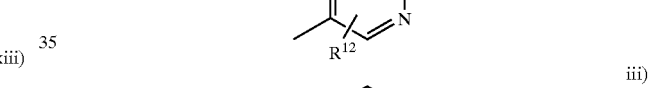

iv)
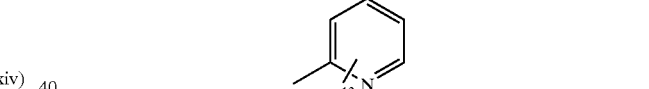

v)
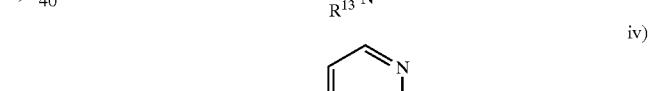

vi)
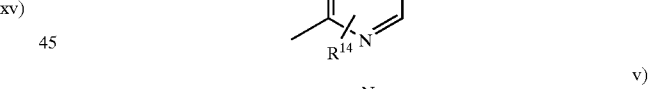

vii)
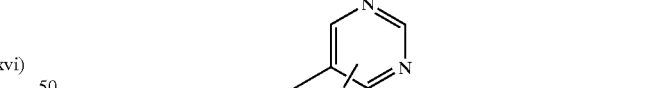

viii)
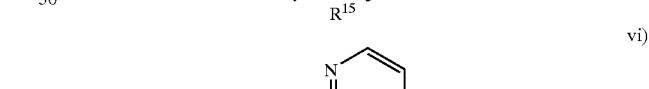

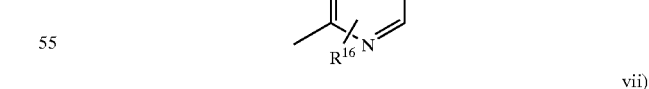

ix) 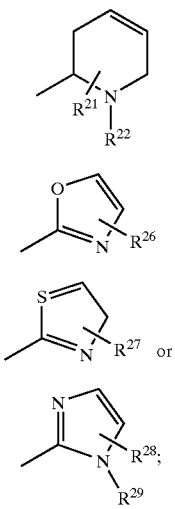

xiii)

xiv)

xv)

Most preferably —E represents i)

iv)

vii) 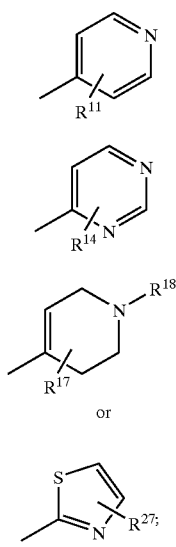

xiv)

Further preferred example of particular values for —E is a heterocycle of the formula i) 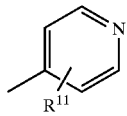

—A—E can be attached to the 1 or the 2 position of the naphthalene ring. Preferably —A—E is attached to the 2 position of the naphthalene ring.

It will be appreciated that when p is other than zero, then the $R^1$ substituents can be different. Similarly, when q is other than zero, then the $R^2$ substituents can be different.

$R^1$ is preferably selected from $C_1$–$C_6$ alkyl, $C_1$–$C_6$ alkoxy halogen, trifluoromethyl.

$R^2$ is preferably selected from $C_1$–$C_6$ alkyl, $C_1$–$C_6$ alkoxy halogen, trifluoromethyl.

When —A—E is attached to the 2 position of the naphthalene ring, p is 1 or 2 it is preferred that one $R^2$ group is attached to the 1 position of the naphthalene ring.

Preferred compounds are those having one or more or any combination of the following features:

a) p is 2;
b) p is 1;
c) p is 0;
d) q is 2;
e) q is 1;
f) q is 0;
g) $R^1$ is selected from $C_1$–$C_6$ alkyl, $C_1$–$C_6$ alkoxy halogen or trifluoromethyl;
h) $R^2$ is selected from $C_1$–$C_6$ alkyl, $C_1$–$C_6$ alkoxy halogen or trifluoromethyl;
i) $R^2$ is $C_1$–$C_6$ alkoxy, especially methoxy;
j) —E is a heterocycle selected from:

i) 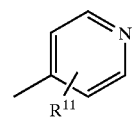

iv) 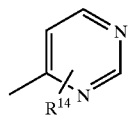

vii) 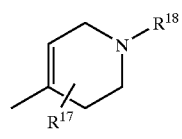

or xiv) 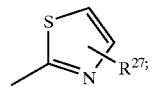

k) $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$ and $R^{32}$ are each independently selected from $C_1$–$C_6$ alkyl, especially methyl, $C_1$–$C_6$ alkoxy, especially methoxy, halogen, especially chloro and fluoro, trifluoromethyl, amino, a substituted or unsubstituted phenyl, and a substituted or unsubstituted phenoxy;
l) —A— is —$CR^5$=$CR^6$—;
m) $R^5$ is hydrogen;
n) $R^6$ is hydrogen;
o) —A— is —$CHR^3$—$CHR^4$—;
p) $R^3$ is hydrogen;
q) wherein $R^4$ is hydrogen;
r) —A— is —C≡C;
s) —A— is —COO—;
t) —A—E is attached to the 1 position of the naphthalene ring;
u) —A—E is attached to the 2 position of the naphthalene ring;
v) —A—E is attached to the 1 position of the naphthalene ring, p is 2 or 1 and one $R^2$ group is attached to the 2 position of the naphthalene ring;
w) —A—E is attached to the 1 position of the naphthalene ring, p is 2 or 1 and one $R^2$ group is attached to the 3 position of the naphthalene ring;

x) —A—E is attached to the 1 position of the naphthalene ring, p is 2 or 1 and one $R^2$ group is attached to the 4 position of the naphthalene ring;
y) —A—E is attached to the 2 position of the naphthalene ring, p is 2 or 1 and one $R^2$ group is attached to the 1 position of the naphthalene ring;
z) —A—E is attached to the 2 position of the naphthalene ring, p is 2 or 1 and one $R^2$ group is attached to the 3 position of the naphthalene ring; and
aa) —A—E is attached to the 2 position of the naphthalene ring, p is 2 or 1 and one $R^2$ is attached to the 4 position of the naphthalene ring;

Particularly preferred compounds are of the formula

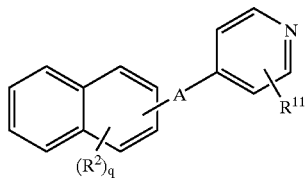

(Ia)

wherein A, E, $R^2$, $R^{11}$ and q are as defined above. More particularly preferred compounds are of the formula

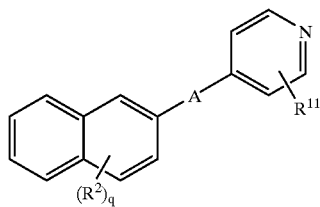

(Ib)

wherein A, $R^2$, $R^{11}$ and q are defined above. Even more particularly preferred compounds are of the formula

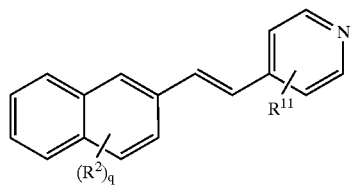

(Ic)

wherein $R^2$, $R^{11}$ and q are defined above. Examples of particularly preferred compounds are of the formula

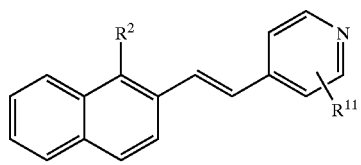

(Id)

wherein $R^2$ and $R^{11}$ are defined above.

Particular examples of the compounds of the invention are

4-[2-(2-(1-methoxy)naphthyl)vinyl]pyridine,
4-[2-(2-(1-methoxy)naphthyl)ethyl]pyridine,
4-[2-(2-(1-ethoxy)naphthyl)vinyl]pyridine,
4-[2-(2-(1-propyloxy)naphthyl)vinyl]pyridine hydrochloride,
4-[2-(2-(1-ethoxycarbonylmethyl)oxy)naphthyl)vinyl] pyridine,
4-[2-(2-(1-(methoxyethoxy)naphthyl)vinyl]pyridine, hydrochloride,
4-[2-(2-(1-(cyclopropylmethyloxy)naphthyl)vinyl]pyridine, hydrochloride,
4-[2-(2-(1-propargyloxy)naphthyl)vinyl]pyridine,
4-[2-(2-(1-bromo)naphthyl)vinyl]pyridine,
4-[2-(2-(1-(thiomethyl)naphthyl)vinyl]pyridine,
4-[2-(2-(1-chloro)naphthyl)vinyl]pyridine,
4-[2-(2-(1-chloro)naphthyl)ethyl]pyridine,
4-[2-(2-(1-cyano)naphthyl)vinyl]pyridine,
4-[2-(2-(1-trifluoromethyl)naphthyl)vinyl]pyridine,
4-[2-(2-(1-nitro)naphthyl)vinyl]pyridine,
4-[2-(2-(3-(methyl)naphthyl)vinyl]pyridine,
4-[2-(2-(3-(chloro)naphthyl)vinyl]pyridine,
4-[2-(2-(3-(thiomethyl)naphthyl)vinyl]pyridine,
4-[2-(2-(3-thiomethyl)naphthyl)ethyl]pyridine,
4-[2-(2-(1-methoxy)naphthyl)vinyl]pyrimidine,
4-[2-(2-naphthyl)vinyl]pyrimidine,
2-[2-(2-(1-methoxy)naphthyl)vinyl]thiazole,
trans-3-fluoro-4-[2-(2-naphthyl)vinyl]pyridine,
cis-3-fluoro-4-[2-(2-naphthyl)vinyl]pyridine,
4-[2-(2-naphthyl)ethynyl]pyridine, and
4'-pyridyl 1-methoxy-2-naphthoate.

The present invention includes pharmaceutically acceptable salts of the formula (I) compounds. These salts can exist in conjunction with an acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterisation or purification.

Certain compounds of formula I are believed to be novel, and are provided as a further aspect of the invention.

Accordingly, the present invention provides novel compounds of general formula:

2. A compound of the formula:

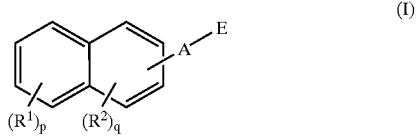

(I)

where p is 0 to 4, q is 0 to 3,
—A— represents a group —CHR$^3$—CHR$^4$—, —CR$^5$=CR$^6$—, —C≡C, or —COO—, wherein R³ is hydrogen or hydroxy, R⁴, R⁵ and R⁶ are each independently hydrogen or $C_1$–$C_6$ alkyl, a substituted or unsubstituted phenyl, carboxy ($C_1$–$C_6$)alkyl or cyano;

—E represents a substituted or unsubstituted heterocycle;

R¹ and R² are each independently selected from $C_1$–$C_6$ alkyl, hydroxy, $C_1$–$C_6$ alkoxy, nitro, cyano, $C_1$–$C_6$ alkylthio, halogen, trifluoromethyl, a substituted or unsubstituted phenyl, a substituted or unsubstituted benzyl or a group represented by —O—(CH$_2$)$_{m'}$—Y, in which Y represents $C_3$–$C_6$ cycloalkyl, $C_2$–$C_6$ alkenyl, $C_2$–$C_6$ alkynyl, a substituted or unsubstituted phenyl, $C_1$–$C_6$ alkoxy, and m' is 0 or 1;

or a pharmaceutically acceptable salt or ester thereof, provided that when m' represents 0, Y does not represent $C_1$–$C_6$ alkoxy;

other than 2-[2-(2-(1-chloro)naphthyl)vinyl]pyridine, 2-[2-(2-(1-bromo)naphthyl)vinyl]pyridine, naphthylvinylpyridine, 4-[2-(2-naphthyl)vinyl]-2-nitropyridine, 4-[2-(2-naphthyl)acetinyl]pyridine, 4-[2-(2-(6-di-(n-butyl)amino)naphthyl)vinyl]pyridine or 4-[2-(2-naphthyl)ethyl]pyridine.

The invention also includes a process for preparing a novel compound according to formula (I) or a pharmaceutically acceptable salt or ester thereof.

1. The compounds of formula (I), where —A— is —CH═CH—, can be made by the following reactions, which comprise (a) reacting a compound of formula

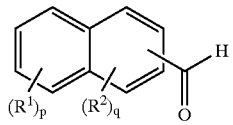

(Ia)

wherein R¹, R², p and q are as defined above, with a compound of formula E—CH₃, wherein E has the values given above, (b) reacting a compound of formula

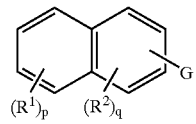

(Ib)

wherein R¹, R², p and q are as defined above, and G is a group of the formula —CH₂—(PO)—(OR')₂ or —CH₂—P(R')₃, wherein R' is a $C_1$–$C_6$ alkyl, with a compound of formula E—CHO wherein E— has the values given above, or, (c) reacting a compound of formula

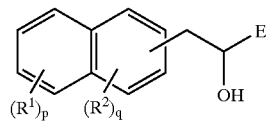

(Ic)

wherein R¹, R², p, q and E— are as defined above, with a suitable reactant such as methanesulphonyl chloride;

The reactions are carried out preferably at a range of temperatures varying from 0° C. up to reflux. It is also preferred in process variants (a) and (c) that the reaction is carried out in the presence of a suitable base such as for example sodium acetate in variant (a) and triethylamine in variant (c). It is further preferred that the reaction is carried out in a suitable organic solvent such as acetic anhydride or dichloromethane;

The intermediates in process variants (a) and (b) are readily available or are synthesized by conventional methods. The intermediate (Ic) is prepared via anionic condesation of the alkyl naphthyl (IIc) with the aldehyde (IIIc) using conventional methods;

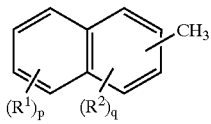

(IIc)

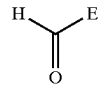

(IIIc)

2. The compounds of formula (I), where —A— is —C≡C—, can be made by the following reaction, which comprises (d) reacting a compound of formula

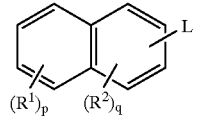

(Id)

wherein p, q, R¹, and R² are as defined above, and L is a suitable leaving group, such as for example an iodo group, with a compound of formula HC≡C—E, wherein —E has the values given above.

The reaction is carried out preferably at a range of temperatures varying from room temperature up to reflux, in the presence of a suitable catalyst, such as for example (PPh₃)₂PdCl₂. It is further preferred that the reaction is carried out in the presence of CuI, in a suitable organic solvent such as triethylamine, used also as a base;

The intermediate HC≡—C—E is synthesized in two steps, using standard procedures, by Palladium catalyst condensation with trimethylsilylacetylene with L—E, wherein L is a leaving group, as defined above, followed by subsequent deprotection using a suitable base such as, for example, K2CO3.

3. The compounds of formula (I), where —A— is —CH₂—CH₂—, can be made by the following reaction, which comprises (e) reducing compounds of formula

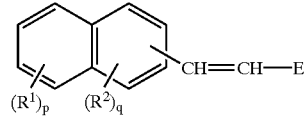

(Ie)

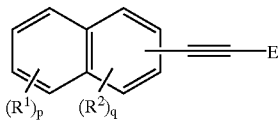

(Ie')

wherein p, q, m, $R^1$, $R^2$ and E are as defined above.

The reaction is carried out preferably at a range of temperatures varying from 0° C. up to room temperature, in the presence of a suitable catalyst, such as for example $PtO_2$/C or Pd/C, in a suitable organic solvent such as ethyl acetate;

The intermediates (Ie) and (Ie') are as shown in process variants (a), (b), (c) and (d).

4. The compounds of formula (I), where —A— is —COO—, or —CO—, can be made by the following reaction, which comprises (f) condensing a compound of formula

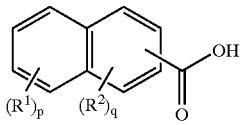

(If)

wherein $R^1$, $R^2$, p and q are as defined above, with a compound of formula E'—OH, wherein E' is a heterocycle substituted with a hydroxyl group and 1 to 2 times with a group $R^4$, wherein $R^4$ is as defined above.

Please note that when E' is a nitrogen containing heterocycle, it can react through the hydroxyl group to give compounds where —A— is —COO—.

The reaction can be carried out using conventional methods, such as in the presence of an acyl chloride, such as for example, oxalyl chloride, or in the presence of a coupling agent, such as for example, dicylohexylcarbodiimide, N,N-carbonyldiimidazole or 2-chloro-1-methylpyridinium iodide. In any instance, the reaction is carried out preferably at a range of temperatures varying from 0° C. up to reflux, optionally in the presence of a suitable base, such as for example, triethylamine, in a suitable organic solvent such as dichloromethane;

The intermediate (If) is readily available or it is synthesized by conventional methods.

5. The compounds of formula (I), where $R^2$ is —O—$(CH_2)_{m'}$—Y, can be made by the following reaction, which comprises (g) reacting a compound of formula

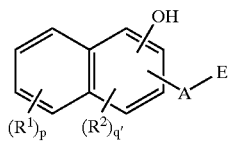

(Ig)

wherein $R^1$, $R^2$, A, p and E are as defined above, and q' is independently 0 or 1, with a compound of formula L'—$(CH_2)_{m'}$—Y, where m' and Y are as defined above, and L' is a suitable leaving group, such as for example iodo, bromo or chloro;

The reaction is carried out preferably at a range of temperatures varying from 0° C. up to room temperature, optionally in the presence of a suitable alkaline base such as for example sodium hydride, in a suitable organic solvent, such as N,N-dimethylformamide;

The intermediate (Ig) is synthesized as shown in process variants above.

It will be appreciated that all these process variants may be optionally followed by the formation of esters or salts thereof.

The present invention further provides the novel starting materials described herein.

The particular effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The activity of compounds according to the invention may be demonstrated in the following test, which involves the electrophysiological characterization of test compounds using HEK293 cells stably expressing human GluR6. The cells may be obtained as described in Hoo, K. H., et al., Receptors Channels 1994, 2, 327–337.

In the test, cells are dissociated by trituration and plated out onto poly-L-lysine coated (10 μg/ml) glass coverslips. Whole-cell voltage clamp recordings (Vh=−70 mV) are made using the tight seal whole cell configuration of the patch-clamp technique (Hamill et al., (1981) Pflügers Arch., 391:85–100). Glass fragments of coverslips with adherent cells are placed in a perfusion chamber, pre-incubated with 250 μg/ml conconavalin A to remove agonist-induced desensitization, and rinsed with buffer of composition: 138 mM NaCl, 5 mM $CaCl_2$, 5 mM KCl, 1 mM $MgCl_2$, 10 mM HEPES and 10 mM glucose, pH of 7.5 with NaOH (osmolality 315 mosm/kg). The recording pipette solutions contain 140 mM CsCl, 1 mM $MgCl_2$, 14 mM HEPES (N-[2-hydroxyethyl]-piperazin-N'-[2-ethanesulfonic acid]) and 15 mM BAPTA (1,2-bis(2-aminophenoxy)ethane-N,N,N',N',-tetraacetic acid ), pH of 7.2 with CsOH (osmolality 295 mosm/kg). Experiments were performed at ambient temperature (20–22° C.) and recorded on either a List EPC-7 or an Axopatch ID amplifier.

Cells were superfused with solution containing agonist (1 mM kainate) in buffer and steady state current values obtained. Agonist in the presence of compound was then applied and the reduction in the inward current from control kainate-induced current measured. The reduction in current produced by the compound was assessed at steady state. Recovery of control currents elicited by kainate (1 μM) was established by repeat application of kainate to the cells via the external solution. The compound tested were evaluated for use-dependency. The recovery from compound inhibition of kainate-induced current was dependent upon the rate of repeat kainate application following antagonist inhibition of currents. In addition, outward currents measured by voltage-clamping at positive potentials (+70 mV) were not inhibited by the compounds whereas inward currents were.

All of the compounds exemplified herein have been found to show activity in this test at a concentration of 30 micromolar or lower.

The compounds of the present invention are preferably formulated prior to administration. Therefore, another aspect of the present invention is a pharmaceutical formulation comprising a compound of formula I or a pharmaceutically acceptable salt thereof, and a pharmaceutically acceptable carrier. The present pharmaceutical formulations are prepared by known procedures using well-known and readily available ingredients. In making the formulations of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Formulations of the invention may be formulated so as to provide quick, sustained, or delayed release of the active ingredient after administration to the patient by employing procedures well known in the art.

The formulations are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutically acceptable carrier.

The following examples are illustrative of compounds for use in the manufacture of a medicament for the treatment of a condition indicating treatment with a GluR6 antagonist.
Materials and Methods.

All solvents and reagents were purchased from commercial sources and used as received, unless otherwise indicated. Tetrahydrofurane (THF) was distilled from sodium benzophenone ketyl prior to use; N-Dimethylformamide (DMF) was dried over 4° molecular sieves; Triethylamine (Et$_3$N) was distilled from calcium hydride. The reactions done with these solvents were performed under a positive pressure of argon. $^1$H-NMR and $^{13}$C-NMR data were recorded on a Bruker AC-200P and a Varian Unity 300. IR spectra were obtained on Nicolet 510 P-FT and a Perkin Elmer 883 (KBr). Melting points were determined on a Electrothermal IA6304 apparatus and are not corrected. MS spectra were recorded on a Hewlett-Packard 5988A (70 eV) utilizing chemical ionization (CI). Analytical TLC was performed on Merck TLC glass plates precoated with F$_{254}$ silica gel 60 (UV, 254 nm and Iodine). Chromatographic separations were performed by using 230–400 mesh silica gel (Merck).

EXAMPLE 1

Synthesis of 4-[2-(2-(1-methoxy)naphthyl)vinyl]pyridine (3)

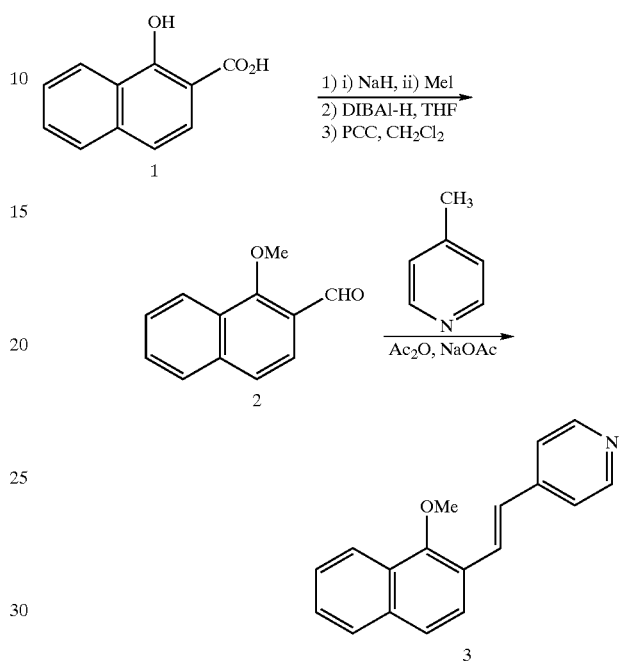

To a suspension of NaH (95%, 590 mg., 23.38 mmol.) in 20 ml of DMF is added, portionwise, the acid 1 (2 g., 10.63 mmol.) at 0° C. The resulting mixture is stirred at this temperature during 30 m. and, then, 1.45 ml. (23.38 mmol.) of methyl iodide are added. The reaction is maintained for 2 h., quenched with H$_2$O and extracted with CH$_2$Cl$_2$. The organic phase is dried over Na$_2$SO$_4$, filtered and evaporated to dryness. It is obtained a pale yellow residue which is solved in 10 ml of THF and treated, at 0° C., with 27.8 ml (27.8 mmol.) of a 1 M solution of Dibal-H in THF. After the addition, the reaction is stirred at room temperature overnight and quenched, at 0° C., with a saturated solution of NH$_4$Cl. Then, it is extracted with CH$_2$Cl$_2$ and the organic phase washed with H$_2$O, dried over Na$_2$SO$_4$ and evaporated to dryness. The crude product is purified by flash chromatography using hexane/EtOAc (1:1) as eluent, yielding a white solid. This solid is solved in 30 ml. of CH$_2$Cl$_2$ and treated with 2.45 g. (11.2 mmol.) of PCC. The mixture is stirred at room temperature for 1 h. Then, it is filtered off through celite and the celite washed three times with CH$_2$Cl$_2$. The filtrate is evaporated to dryness and the residue is purified by flash chromatography using hexane/EtOAc (9:1) as eluent. It was obtained 2 (1.3 g., 67%) as a white solid. To a suspension of 550 mg. (2.95 mmol.) of 2 and 485 mg. (5.91 mmol.) of NaOAc in 5 ml. of Ac$_2$O are added 280 mg. (2.95 mmol.) of 4-Picoline and the mixture heated at reflux. After 4 h. it is added another equivalent of 4-Picoline and the reaction heated overnight. Once the reaction is cooled to room temperature, it is treated with a saturated solution of NaHCO$_3$ until pH=8. Then, the aqueous phase is extracted twice with CH$_2$Cl$_2$ and the organic phase is dried over Na$_2$SO$_4$, filtered off and evaporated to dryness. The black residue is purified by flash chromatography using hexane/EtOAc (1:1) as eluent, yielding 3 as a pale brown solid. MS (CI): 262 (M$^+$+1, 100).

EXAMPLE 2

Synthesis of 4-[2-(2-(1-methoxy)naphthyl)ethyl]pyridine] (4)

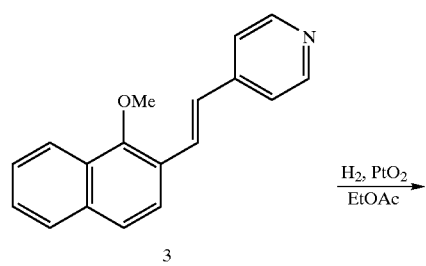

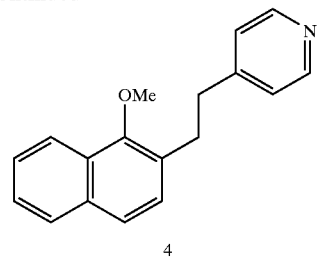

A mixture of 40 mg. (0.153 mmol.) of 3 and 14 mg. (0.062 mmol.) of PtO$_2$ in 5 ml. of EtOAc is treated with H$_2$ (balloon pressure) during 4 h. at room temperature. Then, the reaction is filtered off through celite. The celite is washed twice with EtOAc and the filtrate is evaporated to dryness. The residue is purified by flash chromatography using EtOAc as eluent, affording 33 mg. (82%) of 4 as a transparent oil. The oil is solved in Et$_2$O and treated with 1 ml of a saturated solution of HCl in Et$_2$O to isolate the hydrochloride of 4 as a white solid. MS (CI): 264 (M$^+$+1, 100).

EXAMPLE 3

General Procedure for the Synthesis of the Ether Derivatives

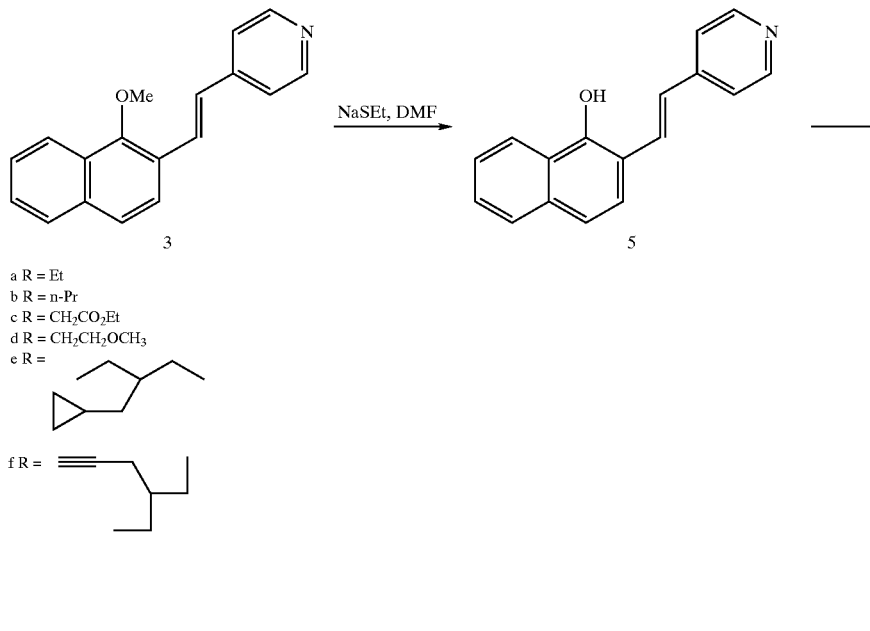

a R = Et
b R = n-Pr
c R = CH$_2$CO$_2$Et
d R = CH$_2$CH$_2$OCH$_3$
e R = f R =

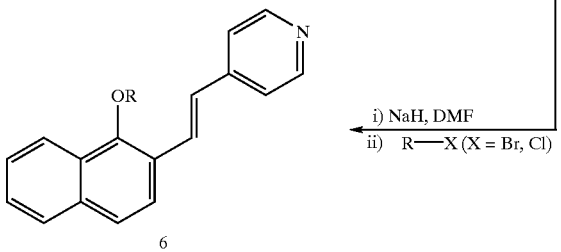

A solution of 1.08 g. (4.1 mmol.) of 3 and 840 mg. (10 mmol.) of sodium thioethoxide in 10 ml. of DMF is heated at 100° C. over 2 h. Then, the reaction mixture is cooled down to 0° C. and treated with a 2M solution of HCl. The generated precipitated is filtered off and washed with H₂O and Et₂O, yielding the phenol 5 as a pale brown solid in a 83% yield. A solution of the phenol 5 (0.7 mmol.) in 6 ml. of DMF is treated, at 0° C., with NaH (2 equiv.). The reaction mixture is stirred at room temperature for 30 m. and, then, the corresponding alkylating agent (1.1 equiv.) is added. The mixture is stirred during 20 h., quenched with a saturated solution of NH₄Cl and extracted with CH₂Cl₂. The organic phase is washed with H₂O, dried over Na₂SO₄ and evaporated to dryness. The residue is purified by flash chromatography using EtOAc as eluent, yielding the desired ether 6. The derivatives which are not solid are treated with a saturated solution of HCl in Et₂O in order to generate the corresponding hydrochloride, which is solid in all cases.

4-[2-(2-(1-ethoxy)naphthyl)vinyl]pyridine (6a). MS (CI): 276 (M⁺+1, 100).
4-[2-(2-(1-propyloxy)naphthyl)vinyl]pyridine, hydrochloride (6b). Mp: 190–191° C.
4-[2-(2-(1-(ethoxycarbonylmethyl)oxy)naphthyl)vinyl] pyridine (6c). MS (CI): 334 (M⁺+1, 100).
4-[2-(2-(1-(methoxyethoxy)naphthyl)vinyl]pyridine, hydrochloride (6d). MS (CI): 306 (M⁺+1, 100).
4-[2-(2-(1-(cyclopropylmethyloxy)naphthyl)vinyl]pyridine, hydrochloride (6e). MS (CI): 302 (M⁺+1, 100).
4-[2-(2-(1-propargyloxy)naphthyl)vinyl]pyridine (6f). MS (CI): 286 (M⁺+1, 100).

EXAMPLE 4

Synthesis of 4-[2-(2-(1-bromo)naphthyl)vinyl] pyridine (9)

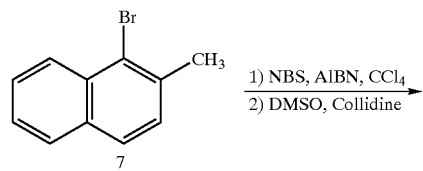

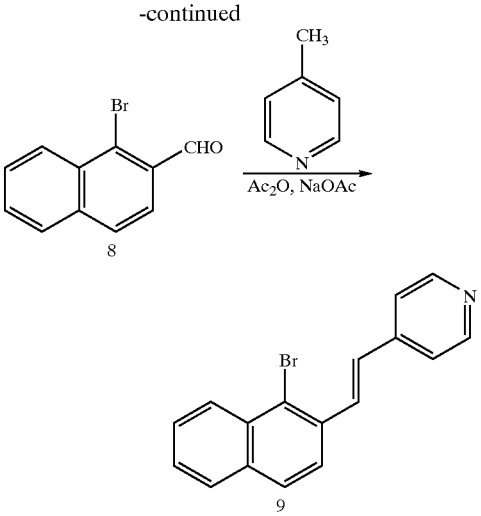

A solution of 11.1 g. (45.23 mmol.) of 1-bromo-2-methylnaphthalene (7), 9.66 g. (54.27 mmol.) of N-Bromosuccinimide (NBS) and 0.9 g. (5.43 mmol.) of AIBN in 50 ml. of dry CCl₄ is refluxed, under argon atmosphere, for 6 h. Then, the reaction is cooled down to room temperature and filtered off. The filtrate is evaporated to dryness and the residue is purified by flash chromatography using hexane as eluent, yielding 9.8 g. (72%) of the desired benzyl bromide as a white solid. A solution of 8 g. (26.66 mmol.) of this bromide and collidine (3.8 ml., 28 mmol.) in 50 ml. of dry DMSO is stirred at room temperature during 5 days. Then, it is added H₂O and the mixture extracted twice with Et₂O. The organic phase is washed with H₂O, dried over Na₂SO₄ and evaporated to dryness. The crude is purified by flash chromatography using toluene as eluent, affording 3 g. (48%) of the aldehyde 8 as a white solid. A suspension of 2 g. (8.51 mmol.) of 8 and 1.4 g. (17 mmol.) of NaOAc in 15 ml. of Ac₂O is treated with 0.83 ml. (8.51 mmol.) of 4-picoline and the mixture heated at reflux over 2 h. After that time, it is added another equivalent of 4-picoline and the reaction maintained overnight at reflux. The reaction is cooled down until 0° C. and neutralised with a saturated solution of NaHCO₃. The aqueous phase isextracted with CH₂Cl₂ and the organic phase is washed with H₂O, dried over Na₂SO₄ and evaporated at vacuum. The crude is purified by flash chromatography using CH₂Cl₂/EtOAc (8:2) as eluent. The desired product 9 was obtained as a pale brown solid. MS (CI): 312 (M⁺+3, 100), 310 (M⁺+1, 81).

EXAMPLE 5

Synthesis of the Derivatives 10

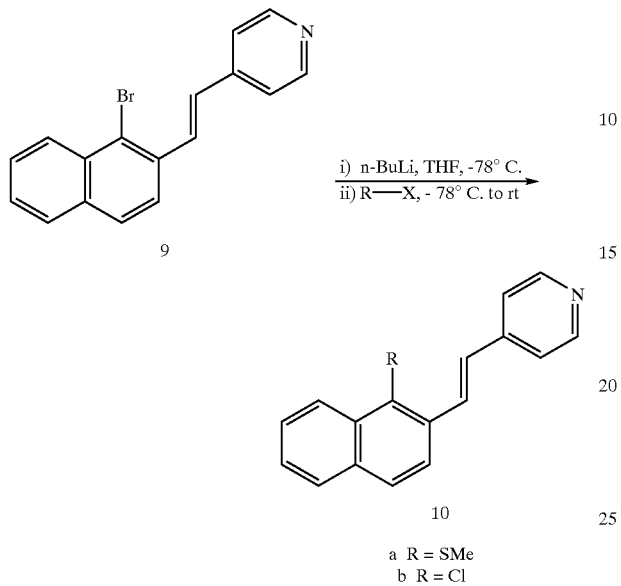

a  R = SMe
b  R = Cl

A solution of 0.5 mmol. of 9 in 3 ml. of THF is treated, at −78° C., with a 1.6M solution of n-BuLi in hexane (1.1 equiv.) After 30 m., it is added the corresponding electrophile (2 equiv.) and the reaction mixture slowly warmed-up until room temperature. Then, it is quenched with a saturated solution of NH$_4$Cl and extracted with CH$_2$Cl$_2$. The organic phase is dried over Na$_2$SO$_4$, filtered off and evaporated to dryness. The residue is purified by flash chromatography using CH$_2$Cl$_2$/EtOAc (8:2) as eluent and yielding the desired product 10 as a white solid.

4-[2-(2-(1-(thiomethyl)naphthyl)vinyl]pyridine (10a). MS (CI): 278 (M$^+$+1, 100).

4-[2-(2-(1-chloro)naphthyl)vinyl]pyridine (10b). MS (CI): 268 (M$^+$+3, 33), 266 (M$^+$+1, 100), 232 (M$^+$+2−Cl, 12).

EXAMPLE 6

Synthesis of 4-[2-(2-(1-chloro)naphthyl)ethyl]pyridine (11)

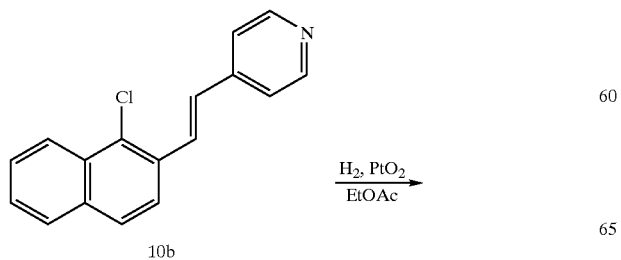

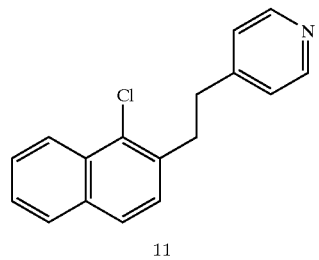

A mixture of 50 mg. (0.188 mmol.) of 10b and 15 mg. (0.063 mmol.) of PtO$_2$ in 5 ml. of EtOAc is treated with H$_2$ (balloon pressure) during 5 h. at room temperature. Then, the reaction is filtered off through celite. The celite is washed twice with EtOAc and the filtrate is evaporated to dryness. The residue is purified by flash chromatography using EtOAc as eluent, yielding 11 as a pale brown solid. MS (CI): 270 (M$^+$+3, 37), 268 (M$^+$+1, 100), 234 (9).

EXAMPLE 7

Synthesis of 4-[2-(2-(1-cyano)naphthyl)vinyl]pyridine (12)

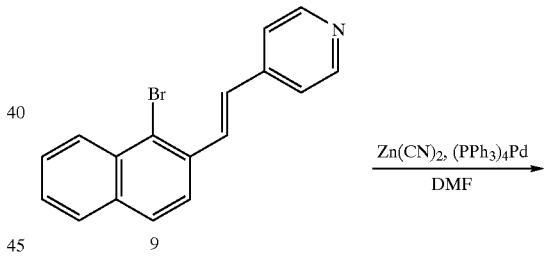

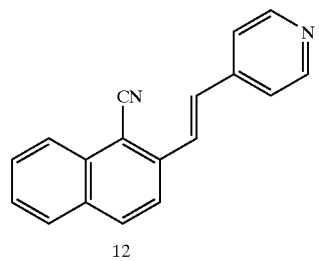

A suspension of 80 mg. (0.26 mmol.) of 9, 18 mg. (0.01 mmol.) of (PPh$_3$)$_4$Pd and 22 mg. (0.19 mmol.) of Zn(CN)$_2$ in 1 ml. DMF is heated in a sealed tube, at 120° C., for a week. Then, the reaction mixture is cooled down to room temperature, poured into a 5% solution of NaOH and extracted with $CH_2Cl_2$. The organic phase is dried over $Na_2SO_4$, filtered off and evaporated at vacuum. The crude is purified by flash chromatography using EtOAc as eluent, yielding 12 as a pale brown solid. MS (CI): 257 ($M^++1$, 100).

EXAMPLE 8

Synthesis of 4-[2-(2-(1-trifluoromethyl)naphthyl) vinyl]pyridine (16)

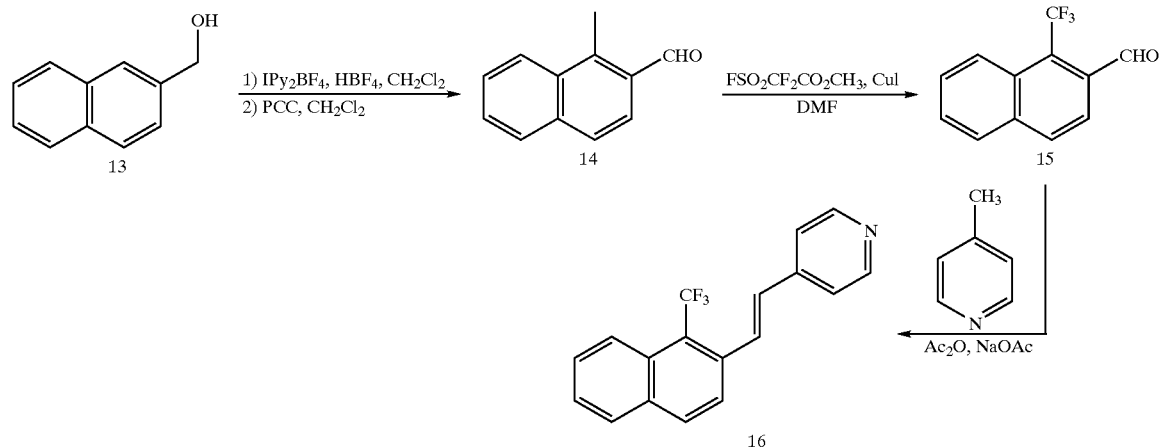

A solution of 5 g. (31.6 mmol.) of 13 in 30 ml of $CH_2Cl_2$ is treated, at room temperature, with Iodo-bis-pyridinium tetrafluoroborate (1.1 equiv.) and tetrafluoroboric acid (1 equiv.). After 1.5 h., the reaction is poured into $H_2O$ and extracted with more $CH_2Cl_2$. The organic phase is dried over $Na_2SO_4$, filtered off and evaporated to dryness. The crude mixture is purified by flash chromatography using $CH_2Cl_2$/MeOH (97:3) as eluent, affording the desired iodo-derivative as a brown solid (2.7 g., 30%). A solution of 2 g. (7.05 mmol.) of the iodo-derivative in 20 ml. of $CH_2Cl_2$ is treated with 2.27 g. (10.56 mmol.) of PCC at room temperature. After 1 h., the reaction mixture is filtered off through celite. The celite is washed three times with $CH_2Cl_2$ and the combined organic extracts are evaporated at vacuum. The residue is purified by flash chromatography using toluene as eluent, yielding 1.7 g. (86%) of 14 as a pale yellow solid. A suspension of 200 mg. (0.709 mmol.) of 14, 80 mg. (0.420 mmol.) of CuI and 181 µL (1.42 mmol.) of methyl 2,2-difluoro-2-(fluorosulfonyl)acetate in 4 ml. of DMF is heated, at 100° C., for 7 h. in a sealed tube. Then, the reaction mixture is cooled down to room temperature, poured into $H_2O$ and extracted with $Et_2O$. The organic phase is dried over $Na_2SO_4$, filtered off and evaporated to vacuum. The crude mixture is purified by flash chromatography using hexane/toluene (8:2) as eluent, affording 114 mg. (72%) of 15 as a transparent oil. To a suspension of 95 mg. (0.424 mmol.) of 15 in 2 ml. of $Ac_2O$ are added 45 µL (0.424 mmol.) of 4-picoline and the reaction mixture heated, under argon atmosphere, at reflux for 4 h. Another equivalent of 4-picoline is added and the reaction maintained along 16 h. Then, the mixture is cooled down to 0° C., neutralised with a saturated solution of $NaHCO_3$ and extracted with $CH_2Cl_2$. The organic phase is dried over $Na_2SO_4$, filtered off and evaporated to dryness. The residue is purified by flash chromatography using hexane/toluene (6:4) as eluent. It is obtained 16 as a brown solid. MS (CI): 300 ($M^++1$, 100), 246 (6), 178 (7).

EXAMPLE 9

Synthesis of 4-[2-(2-(1-nitro)naphthyl)vinyl] pyridine (19)

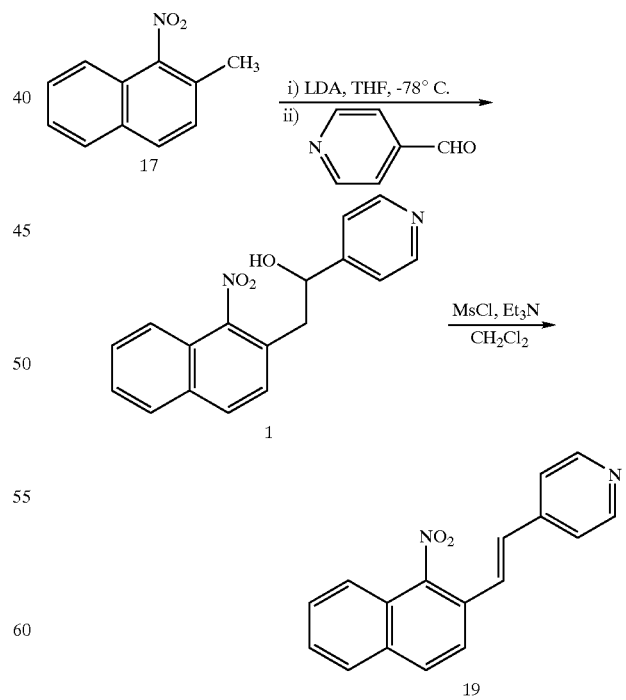

A solution of 1.6 ml. (11.2 mmol.) of di-isopropylamine in 10 ml. of THF is treated, at 0° C., with 6.8 ml. (11 mmol.) of a 1.6M solution of n-BuLi in hexane. After 45 m., this mixture is added, "via cannula", to a solution of 2 g. (10.7 mmol.) of 17 in 20 ml. of THF, at −78° C. The reaction mixture become deep green. One hour later, it is added 4-pycolylcarbaldehyde (1.1 ml., 11.2 mmol.) and the reaction is slowly warmed-up until room temperature. Then, it is quenched with a saturated solution of NH$_4$Cl, poured into H$_2$O and extracted with CH$_2$Cl$_2$. The organic phase is dried over Na$_2$SO$_4$, filtered off and evaporated to dryness. The crude is purified by flash chromatography using CH$_2$Cl$_2$/EtOAc (1:1) as eluent, affording 1.5 g. (48%) of 18 as a white solid. A solution of 500 mg. (1.7 mmol.) of 18 and 1.2 ml. (8.5 mmol.) of Et$_3$N in 5 ml. of CHCl$_3$ is treated with 0.2 ml. (2.5 mmol.) of mesyl chloride and the mixture heated at reflux for 24 h. Once the reaction gets room temperature, it is poured into a saturated solution of NaHCO$_3$ and extracted with CH$_2$Cl$_2$. The organic phase is dried over Na$_2$SO$_4$, filtered off and evaporated at vacuum. The residue is purified by flash chromatography using EtOAc as eluent, yielding 19 as a pale brown solid. MS (CI): 277 (M$^+$+1, 100), 245 (12).

EXAMPLE 10

Synthesis of the Derivatives 22

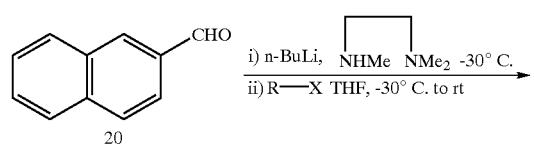

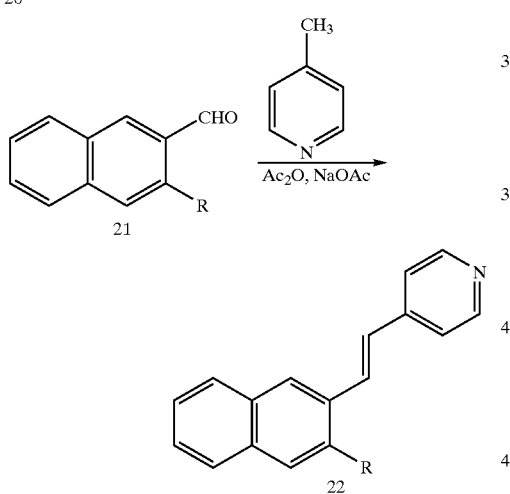

a R = Me
b R = Cl
c R = SMe

A solution of 1.8 ml. (14 mmol.) of trimethylethylenediamine in 35 ml. of THF is treated, at −30° C., with 8.4 ml. (13.4 mmol.) of a 1.6M solution of n-BuLi in hexane. After 15 m., it is added a solution of 2 g.(12.8 mmol.) of 2-naphthaldehyde (20) in 5 ml. of THF and the reaction mixture maintained at −30° C. for 15 m. Then, it is treated with 24 ml. (38.4 mmol.) of a 1.6M solution of n-BuLi in hexane and the temperature maintained along 3 h. After that time, a solution of the corresponding electrophile (5 equiv.) in THF is added and the reaction is slowly warmed-up to room temperature along 2 h. Finally, the reaction is poured into a 10% solution of HCl and extracted with Et$_2$O. The organic phase is washed with H$_2$O, dried over Na$_2$SO$_4$, filtered off and evaporated to dryness. The residue is purified by flash chromatography using hexane/EtOAc (9.5:0.5) as eluent. It is obtained the desired aldehyde 21 as a solid with yields between 60–15%. A suspension of the corresponding aldehyde 21 (4 mmol.) and NaOAc (2 equiv.) in 10 ml. of Ac$_2$O is treated with 4-pycoline (1 equiv.) and the reaction heated, under argon atmosphere, at reflux for 4 h., when it is added another equivalent of 4-pycoline. Then, the mixture is maintained at reflux for 20 h. Once the reaction gets room temperature, it is poured into a saturated solution of NaHCO$_3$ and extracted with CH$_2$Cl$_2$. The aqueous phase is washed with CH$_2$Cl$_2$ and the combined organic extracts are dried over Na$_2$SO$_4$, filtered off and evaporated to dryness. The residue is purified by flash chromatography using hexane/EtOAc (1:1) as eluent, affording 22 as a solid.

4-[2-(2-(3-(methyl)naphthyl)vinyl]pyridine (22a). MS (CI): 246 (M$^+$+1, 100), 178 (5).

4-[2-(2-(3-(chloro)naphthyl)vinyl]pyridine (22b). MS (CI): 268 (M$^+$+3, 46), 266 (M$^+$+1, 100).

4-[2-(2-(3-(thiomethyl)naphthyl)vinyl]pyridine (22c). MS (CI): 278 (M$^+$+1, 100).

EXAMPLE 11

Synthesis of 4-[2-(2-(3-thiomethyl)naphthyl)ethyl]pyridine (23)

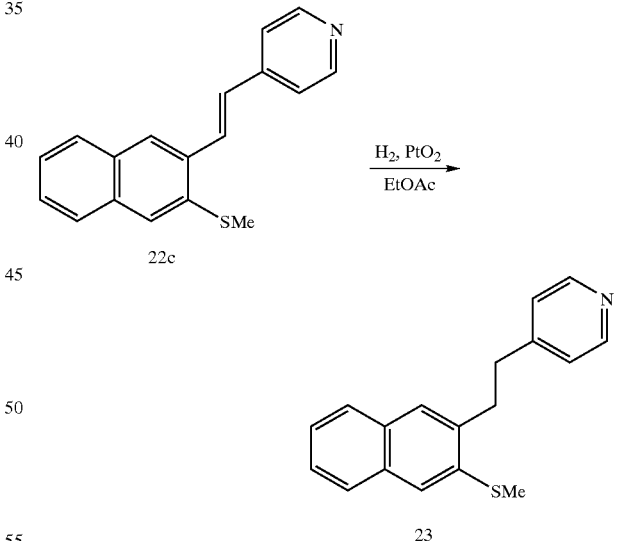

A mixture of 30 mg. (0.11 mmol.) of 22c and 15 mg. (0.063 mmol.) of PtO$_2$ in 5 ml. of EtOAc is treated with H$_2$ (balloon pressure) during 20 h. at room temperature. Then, the reaction is filtered off through celite. The celite is washed twice with EtOAc and the filtrate is evaporated to dryness. The residue is purified by flash chromatography using EtOAc as eluent, affording 23 as a white solid. IR (KBr): 2925, 1594, 1416, 874, 812, 747 cm$^{-1}$.

EXAMPLE 12

Synthesis of the Derivatives 24

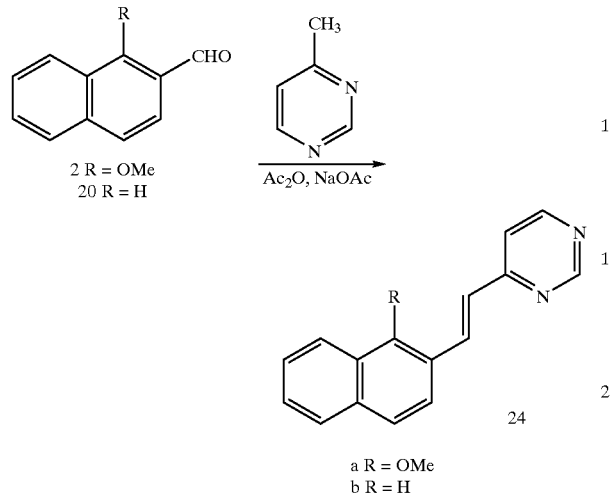

2 R = OMe
20 R = H a R = OMe
b R = H

A suspension of 1.5 mmol. of the corresponding aldehyde (2, 20) and NaOAc (2 equiv.) in 3 ml. of Ac$_2$O is treated with 4-methylpyrimidine (1 equiv.) and the reaction heated, under argon atmosphere, at reflux for 20 h. Once the reaction gets room temperature, it is poured into a saturated solution of NaHCO$_3$ and extracted with CH$_2$Cl$_2$. The aqueous phase is washed with CH$_2$Cl$_2$ and the combined organic extracts are dried over Na$_2$SO$_4$, filtered off and evaporated at vacuum. The crude is purified by flash chromatography using CH$_2$Cl$_2$/EtOAc (1:1) as eluent, affording 24 as a solid.

4-[2-(2-(1-methoxy)naphthyl)vinyl]pyrimidine (24a). MS (CI): 263 (M$^+$+1, 100).
4-[2-(2-naphthyl)vinyl]pyrimidine (24b). MS (CI): 233 (M$^+$+1, 100).

EXAMPLE 13

Synthesis of 2-[2-(2-(1-methoxy)naphthyl)vinyl]thiazole (27)

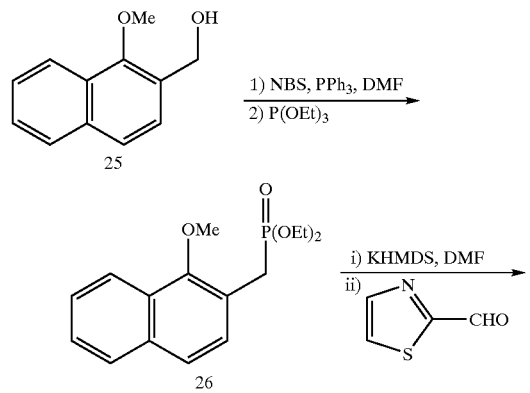

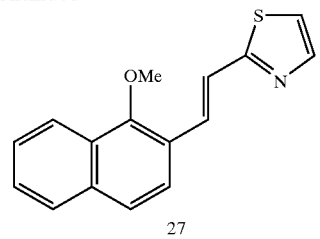

27

To a suspension of 1.9 g. (10 mmol.) of 25 (obtained from 1 after steps 1 and 2) and 4 g. (15 mmol.) of PPh$_3$ in 15 ml. of DMF is added, portionwise, 2.6 g. (14.5 mmol.) of NBS. The mixture is heated at 50° C. for 15 m. Then, the reaction is cooled down to room temperature and quenched with 3.5 ml. of methanol. After 10 m., the reaction mixture is poured into H$_2$O and extracted with Et$_2$O. The organic phase is subsequently washed with a saturated solution of Na$_2$CO$_3$, H$_2$O and brine. Then, it is dried over Na$_2$SO$_4$, filtered off and evaporated at vacuum. The residue is purified by flash chromatography using hexane/EtOAc (4:1) as eluent, yielding the desired brominated derivative as a white solid (1.25 g., 50%). A suspension of 1 g. (4 mmol.) of the brominated derivative in 1 ml. of P(OEt)$_3$ is heated at 120° C., under argon atmosphere, for 2 days. Once the reaction gets room temperature, it is added H$_2$O and the mixture extracted with CH$_2$Cl$_2$. The organic phase is dried over Na$_2$SO$_4$, filtered off and evaporated to dryness. The residue is purified by flash chromatography using CH$_2$Cl$_2$/EtOAc (1:1) as eluent, yielding 900 mg. (75%) of 26 as a white solid. A suspension of 77 mg. (0.25 mmol.) of 26 in 1 ml. of DMF is treated, at 0° C., with a solution of 55 mg (0.27 mmol.) of KHMDS in 1 ml. of DMF. The reaction mixture is maintained at this temperature for 20 m. and, then, a solution of 28 mg. (0.25 mmol.) of 2-thiazolecarboxaldehyde in 1 ml. of DMF is added. The reaction is warmed-up to room temperature and maintained at this temperature during 1 h. After that, it is quenched with a saturated solution of NH$_4$Cl, poured into H$_2$O and extracted with CH$_2$Cl$_2$. The organic phase is dried over Na$_2$SO$_4$, filtered off and evaporated to dryness. The crude is purified by flash chromatography using CH$_2$Cl$_2$/EtOAc (1:1) as eluent, affording 20 mg. (30%) of 27 as a pale yellow oil. In order to get a solid, 27 is solved in 1 ml. of Et$_2$O and treated with 1 ml. of a saturated solution of HCl in Et$_2$O. The formed hydrochloride of 27 is filtrated and washed with Et$_2$O, yielding pure 27, as a pale yellow solid. MS (CI): 268 (M$^+$+1, 100).

EXAMPLE 14

Synthesis of cis and trans 3-Fluoro-4-[2-(2-naphthyl)vinyl]pyridines 30

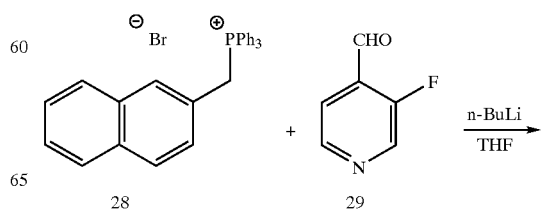

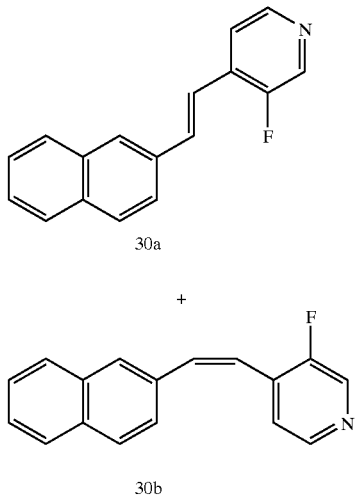

A suspension of 0.46 g. (1.15 mmol.) of 28 (obtained from 2-(bromomethyl)naphthalene by treatment with PPh₃) in 4 ml. of THF is treated, at 0° C., with 0.75 ml. (1.21 mmol.) of a 1.6M solution of n-BuLi in hexane. The reaction is maintained at this temperature for 1 h. and, then, a solution of 0.14 g. (1.1 mmol.) of 29 (obtained from 3-fluoropyridine in a single step, applying a standard procedure) in 2 ml. of THF is added. After the addition, the mixture is warmed-up to room temperature and maintained along 3 h. Then, the reaction is quenched with a saturated solution of $NH_4Cl$, poured into a saturated solution of $NaHCO_3$ and extracted with $CH_2Cl_2$. The organic extracts are dried over $Na_2SO_4$, filtered off and evaporated at vacuum. The crude is purified by flash chromatography using $CH_2Cl_2$/hexane (4:1) as eluent, affording 70 mg. of 30a as a pale yellow oil and 50 mg. of 30b as a pale yellow solid, in a combined yield of 72%. The isomer 30a was transformed into the hydrochloride derivative in order to get a solid.

Trans-3-Fluoro-4-[2-(2-naphthyl)vinyl]pyridine Hydrochloride (30a). MS (CI): 250 ($M^+$+1, 100).
Cis-3-Fluoro-4-[2-(2-naphthyl)vinyl]pyridine (30b). MS (CI): 250 ($M^+$+1, 100)

EXAMPLE 15

Synthesis of 4-[2-(2-naphthyl)ethyl]pyridine (34)

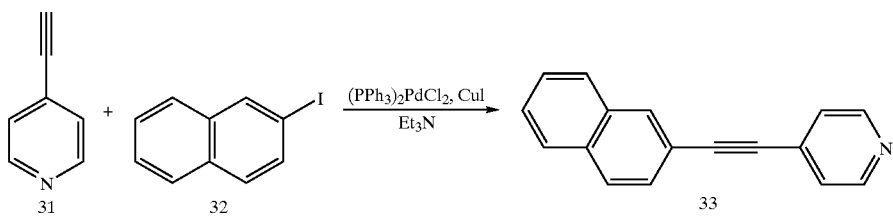

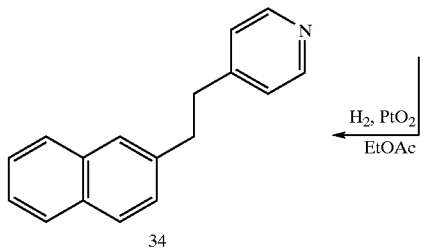

i) A suspension of 90 mg. (0.87 mmol.) of 31 (obtained from 4-bromopyridine in two steps, using standard procedures, by Palladium catalyst condensation with trimethylsilylacetylene and subsequent deprotection with $K_2CO_3$), 220 mg. (0.87 mmol.) of 32, 17 mg. (0.087 mmol.) of CuI and 31 mg. (0.043 mmol.) of $(PPh_3)_2PdCl_2$ in 5 ml. of $Et_3N$ is stirred, under argon atmosphere, at room temperature for 4 h. Then, the reaction is evaporated to dryness and the crude mixture is treated with $CH_2Cl_2$ and $H_2O$. The organic phase is dried over $Na_2SO_4$, filtered off and evaporated at vacuum. The residue is purified by flash chromatography using hexane/EtOAc (7:1) as eluent, affording 33 as a brown solid. MS (CI): 230 ($M{++}1$, 93), 229 ($M+$, 100), 228 ($M+-1$, 41), 227 ($M+-2$, 77), 230 ($M+-3$, 87).

ii) A mixture of 45 mg. (0.20 mmol.) of 33 and 5 mg. (0.02 mmol.) of $PtO_2$ in 2 ml. of EtOAc is treated with $H_2$ (balloon pressure) during 5 h. at room temperature. Then, the reaction is filtered off through celite. The celite is washed twice with EtOAc and the combined organic extracts evaporated to dryness. The residue is purified by flash chromatography using hexane/EtOAc (1:1) as eluent, yielding 34 as a white solid. MS (CI): 235 ($M^++2$, 66), 234 ($M^++1$, 86), 233 ($M^+$, 14), 232 ($M^+-1$, 100), 231 ($M^+-2$, 77).

EXAMPLE 16

Synthesis of the Derivative 36

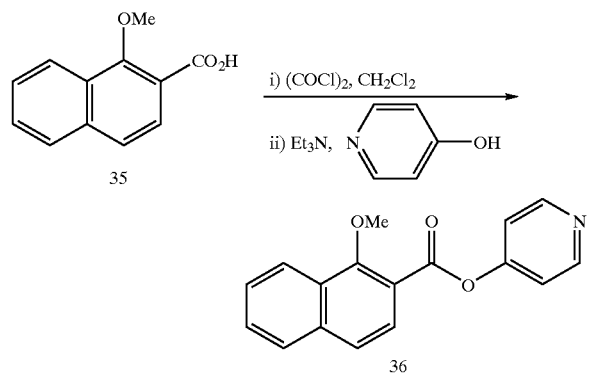

A solution of 150 mg. (0.74 mmol.) of 35 (obtained from 1 in two steps) in 5 ml. of $CH_2Cl_2$ is treated with 0.4 ml. (0.82 mmol.) of a 2M solution of oxalyl chloride in $CH_2Cl_2$ and heated at reflux for 1 h. Once the reaction mixture gets room temperature, it is treated subsequently with 0.22 ml. (1.48 mmol.) of $Et_3N$ and 77 mg. (0.82 mmol.) of 4-hydroxypyridine. The mixture is stirred during 20 h., quenched with a saturated solution of $NH_4Cl$ and poured into $H_2O$. It is extracted with more $CH_2Cl_2$ and the organic extracts are dried over $Na_2SO_4$, filtered off and evaporated to dryness. The residue is purified by flash chromatography using EtOAc as eluent, affording 36, as a white solid.

4'-Pyridyl 1-methoxy-2-naphthoate (36). MS (CI): 280 ($M^++1$, 100), 202 (5).

Formulation 1

Hard Gelatin Capsules Are Prepared Using the Following Ingredients

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets Each Containing 60 mg of Active Ingredient Are Made As Follows

|  |  |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°C and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The following Examples illustrate the invention. In the Examples, $Et_2O$ signifies diethylether, AcOEt signifies ethyl acetate, MeOH signifies methanol, THF signifies tetrahydrofuran, DMF signifies dimethylformamide, and Jones Reagent signifies a solution of 1.0 g of $Na_2Cr_2O_7.2H_2O$ and 1.34 g of sulfuric acid in $H_2O$ (total volume 5 ml.

What is claimed is:

1. A method of treating neurological disorders comprising administrating to a patient in need thereof an effective amount of a compound of the formula:

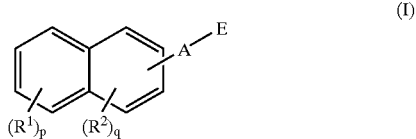

where
p is 0 to 4, q is 0 to 3;
—A—E is attached to the 2 position of the naphthalene ring;
—A— represents a group —CR$^5$=CR$^6$—, or —COO—;
R$^5$ and R$^6$ are each independently hydrogen or C$_1$–C$_6$ alkyl, a substituted or unsubstituted phenyl, carboxy (C$_1$–C$_6$)alkyl or cyano;
—E represents an unsubstituted pyridine or a substituted pyridine selected from the group consisting of

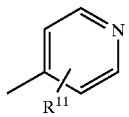 i)

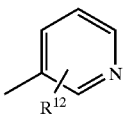 ii)

and

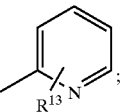 iii)

or an unsubstituted didehydropiperidine; or
a substituted didehydropiperidine selected from the group consisting of

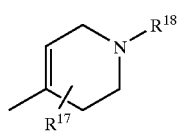 vii)

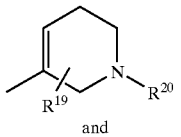 viii)

and

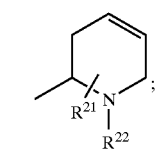 ix)

R$^{11}$, R$^{12}$, R$^{13}$, R$^{17}$, R$^{18}$, R$^{19}$, R$^{20}$, R$^{21}$, and R$^{22}$, are each independently selected from C$_1$–C$_6$ alkyl, especially methyl, C$_1$–C$_6$ alkoxy, especially methoxy and ethoxy, carboxy, hydroxy, cyano, halogen, especially bromo, chloro and fluoro, trifluoromethyl, nitro, amino, C$_1$–C$_6$ acylamino, C$_1$–C$_6$ alkylthio, a substituted or unsubstituted phenyl, a substituted or unsubstituted benzyl and a substituted or unsubstituted phenoxy;
R$^1$ and R$^2$ are each independently selected from C$_1$–C$_6$ alkyl, hydroxy, C$_1$–C$_6$ alkoxy, nitro, cyano, C$_1$–C$_6$ alkylthio, halogen, trifluoromethyl, a substituted or unsubstituted phenyl, a substituted or unsubstituted benzyl or a group represented by —O—(CH$_2$)$_{m'}$—Y, in which Y represents C$_3$–C$_6$ cycloalkyl, C$_2$–C$_6$ alkenyl, C$_2$–C$_6$ alkynyl, a substituted or unsubstituted phenyl, or C$_1$–C$_6$ alkoxy; and m' is 0 or 1;
or a pharmaceutically acceptable salt or ester thereof, provided that when m' represents 0, Y represents C$_3$–C$_6$ cycloalkyl or a substituted or unsubstituted phenyl.

2. The method as claimed in claim 1, wherein p is 2.
3. The method as claimed in claim 1, wherein p is 1.
4. The method as claimed in claim 1, wherein p is 0.
5. The method as claimed in claim 1, wherein q is 2.
6. The method as claimed in claim 1, wherein q is 1.
7. The method as claimed in claim 1, wherein q is 0.
8. The method as claimed in claim 1, wherein R$^1$ is selected from C$_1$–C$_6$ alkyl, C$_1$–C$_6$ alkoxy, halogen or trifluoromethyl.
9. The method as claimed in claim 1, wherein R$^2$ is selected from C$_1$–C$_6$ alkyl, C$_1$–C$_6$ alkoxy, halogen or trifluoromethyl.
10. The method as claimed in claim 9 wherein R$^2$ is C$_1$–C$_6$ alkoxy.
11. The method as claimed in claim 10 wherein R$^2$ is methoxy.
12. The method as claimed in claim 1, wherein —E is selected from the group consisting of:

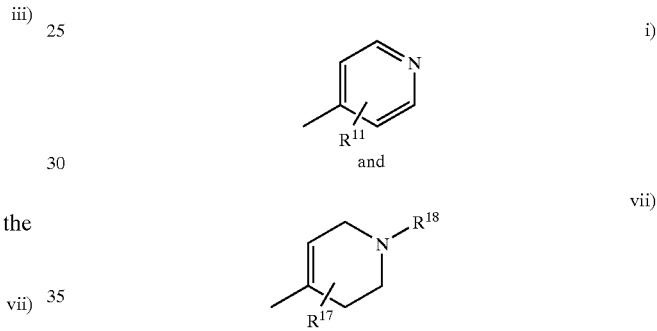

wherein R$^{11}$, R$^{17}$, and R$^{18}$, are each independently selected from C$_1$–C$_6$ alkyl, C$_1$–C$_6$ alkoxy, carboxy, hydroxy, cyano, halogen, trifluoromethyl, nitro, amino, C$_1$–C$_6$ acylamino, C$_1$–C$_6$ alkylthio, a substituted or unsubstituted phenyl, a substituted or unsubstituted benzyl and a substituted or unsubstituted phenoxy.

13. The method as claimed in claim 12, wherein R$^{11}$, R$^{17}$, and R$^{18}$ are each independently selected from C1–C6 alkyl, methyl, C1–C6 alkoxy, methoxy, halogen, chloro and fluoro, trifluoromethyl, amino, a substituted or unsubstituted phenyl, and a substituted or unsubstituted phenoxy.
14. The method as claimed in claim 12, wherein —A— is —CR$^5$=CR$^6$—.
15. The method as claimed in claim 12, wherein R$^5$ is hydrogen.
16. The method as claimed in claim 12, wherein R$^6$ is hydrogen.
17. The method as claimed in claim 12, wherein —A— is —COO—.
18. The method as claimed in claim 12, wherein p is 2 or 1 and one R$^2$ group is attached to the 1 position of the naphthalene ring.
19. The method as claimed in claim 12, wherein p is 2 or 1 and one R$^2$ group is attached to the 3 position of the naphthalene ring.
20. The method as claimed in claim 12, wherein p is 2 or 1 and one R$^2$ is attached to the 4 position of the naphthalene ring.
21. A method of treating neurological disorders comprising administrating to a patient in need thereof an effective amount of a compound of the formula (Ib)

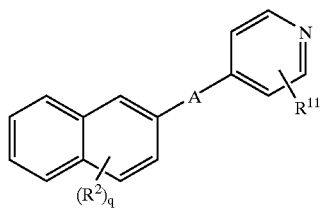

wherein
- —A— represents —CR$^5$=CR$^6$ or —COO—;
- R$^5$ and R$^6$ are each independently hydrogen or C$_1$–C$_6$ alkyl, a substituted or unsubstituted phenyl, carboxy (C$_1$–C$_6$)alkyl or cyano;
- q is 0–3;
- R$^2$ is independently selected from C$_1$–C$_6$ alkyl, hydroxy, C$_1$–C$_6$ alkoxy, nitro, cyano, C$_1$–C$_6$ alkylthio, halogen, trifluoromethyl, a substituted or unsubstituted phenyl, a substituted or unsubstituted benzyl or a group represented by —O—(CH$_2$)$_{m'}$—Y, in which Y represents C$_3$–C$_6$ cycloalkyl, C$_2$–C$_6$ alkenyl, C$_2$–C$_6$ alkynyl, a substituted or unsubstituted phenyl, C$_3$–C$_6$ alkoxy, and m' is 0 or 1;
- provided that when m' represents 0, Y represents C$_1$–C$_6$ cycloalkyl or a substituted or unsubstituted phenyl;
- R$^{11}$ is selected from C$_1$–C$_6$ alkyl, especially methyl, C$_1$–C$_6$ alkoxy, especially methoxy and ethoxy, carboxy, hydroxy, cyano, halogen, especially bromo, chloro and fluoro, trifluoromethyl, nitro, amino, C$_1$–C$_6$ acylamino, C$_1$–C$_6$ alkylthio, a substituted or unsubstituted phenyl, a substituted or unsubstituted benzyl and a substituted or unsubstituted phenoxy.

22. A method of treating neurological disorders comprising administrating to a patient in need thereof an effective amount of a compound of the formula (Ic)

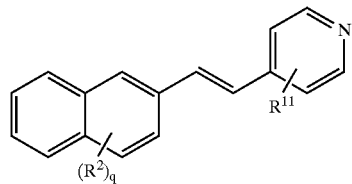

wherein
- q is 0–3;
- R$^2$ is independently selected from C$_1$–C$_6$ alkyl, hydroxy, C$_1$–C$_6$ alkoxy, nitro, cyano, C$_1$–C$_6$ alkylthio, halogen, trifluoromethyl, a substituted or unsubstituted phenyl, a substituted or unsubstituted benzyl or a group represented by —O—(CH$_2$)$_{m'}$—Y, in which Y represents C$_3$–C$_6$ cycloalkyl, C$_2$–C$_6$ alkenyl, C$_2$–C$_6$ alkynyl, a substituted or unsubstituted phenyl, C$_1$–C$_6$ alkoxy, and m' is 0 or 1;
- provided that when m' represents 0, Y represents C$_3$–C$_6$ cycloalkyl or a substituted or unsubstituted phenyl;
- R$^{11}$ is selected from C$_1$–C$_6$ alkyl, especially methyl, C$_1$–C$_6$ alkoxy, especially methoxy and ethoxy, carboxy, hydroxy, cyano, halogen, especially bromo, chloro and fluoro, trifluoromethyl, nitro, amino, C$_1$–C$_6$ acylamino, C$_1$–C$_6$ alkylthio, a substituted or unsubstituted phenyl, a substituted or unsubstituted benzyl and a substituted or unsubstituted phenoxy.

23. A method of treating neurological disorders comprising administrating to a patient in need thereof an effective amount of a compound of the formula (Id)

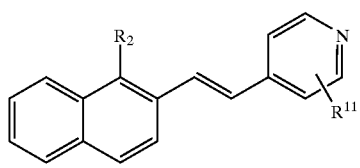

wherein
- R$^2$ is independently selected from C$_1$–C$_6$ alkyl, hydroxy, C$_1$–C$_6$ alkoxy, nitro, cyano, C$_1$–C$_6$ alkylthio, halogen, trifluoromethyl, a substituted or unsubstituted phenyl, a substituted or unsubstituted benzyl or a group represented by —O—(CH$_2$)$_{m'}$—Y, in which Y represents C$_3$–C$_6$ cycloalkyl, C$_2$–C$_6$ alkenyl, C$_2$–C$_6$ alkynyl, a substituted or unsubstituted phenyl, C$_1$–C$_6$ alkoxy, and m' is 0 or 1;
- provided that when m' represents 0, Y represents C$_3$–C$_6$ cycloalkyl or a substituted or unsubstituted phenyl;
- R$^{11}$ is selected from C$_1$–C$_6$ alkyl, especially methyl, C$_1$–C$_6$ alkoxy, especially methoxy and ethoxy, carboxy, hydroxy, cyano, halogen, especially bromo, chloro and fluoro, trifluoromethyl, nitro, amino, C$_1$–C$_6$ acylamino, C$_1$–C$_6$ alkylthio, a substituted or unsubstituted phenyl, a substituted or unsubstituted benzyl and a substituted or unsubstituted phenoxy.

24. The method as claimed in claim 19, wherein R$^2$ is C$_1$–C$_6$ alkoxy.

25. The method as claimed in claim 20, wherein R$^2$ is methoxy.

26. The method as claimed in claim 1 wherein the neurological disorder is epilepsy.

27. A compound of the formula:

(I)

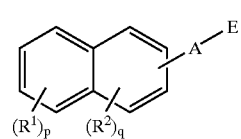

where
- p is 0 to 4, q is 0 to 3;
- —A—E is attached to the 2 position of the naphthalene ring;
- —A— represents a group —CR$^5$=CR$^6$ or —COO—;
- R$^5$ and R$^6$ are each independently hydrogen or C$_1$–C$_6$ alkyl, a substituted or unsubstituted phenyl, carboxy (C$_1$–C$_6$)alkyl or cyano;
- —E represents an unsubstituted pyridine or a substituted pyridine group selected from i)

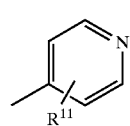

-continued ii)
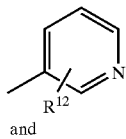
and iii)
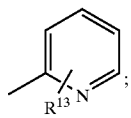;

or an unsubstituted didehydropiperidine; or
a substituted didehydropiperidine group selected from vii)
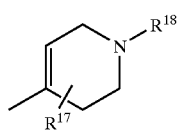

viii)
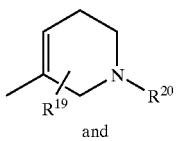
and ix)
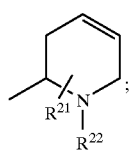;

$R^{11}$, $R^{12}$, $R^{13}$, $R^{17}$, $R^{18}$, $R^{19}$, $R^{20}$, $R^{21}$, and $R^{22}$, are each independently selected from $C_1$–$C_6$ alkyl, especially methyl, $C_1$–$C_6$ alkoxy, especially methoxy and ethoxy, carboxy, hydroxy, cyano, halogen, especially bromo, chloro and fluoro, trifluoromethyl, nitro, amino, $C_1$–$C_6$ acylamino, $C_1$–$C_6$ alkylthio, a substituted or unsubstituted phenyl, a substituted or unsubstituted benzyl and a substituted or unsubstituted phenoxy;

$R^1$ and $R^2$ are each independently selected from $C_1$–$C_6$ alkyl, hydroxy, $C_1$–$C_6$ alkoxy, nitro, cyano, $C_1$–$C_6$ alkylthio, halogen, trifluoromethyl, a substituted or unsubstituted phenyl, a substituted or unsubstituted benzyl or a group represented by —O—$(CH_2)_{m'}$—Y, in which Y represents $C_3$–$C_6$ cycloalkyl, $C_2$–$C_6$ alkenyl, $C_2$–$C_6$ alkynyl, a substituted or unsubstituted phenyl, $C_1$–$C_6$ alkoxy, and m' is 0 or 1;

or a pharmaceutically acceptable salt or ester thereof,
provided that when m' represents 0, Y does not represent $C_1$–$C_6$ alkoxy;
provided when A is —$CR^5$=$CR^6$—, E is unsubstituted 4-pyridyl, q is 0, p is 1 or 2, and at least one $R^2$ group is attached to the 1 position of the naphthalene ring; other than 2-[2-(2-(1-chloro)naphthyl)vinyl]pyridine,
2-[2-(2-(1-bromo)naphthyl)vinyl]pyridine,
naphthylvinylpyridine,
4-[2-(2-naphthyl)vinyl]-2-nitropyridine, or
4-[2-(2-(6-di-(n-butyl)amino)naphthyl)vinyl]pyridine.

28. A pharmaceutical formulation, which comprises a compound as claimed in claim 27 and a pharmaceutically acceptable carrier.

29. A method of treating epilepsy comprising administrating to a patient in need thereof an effective amount of a compound of the formula I as claimed in claim 1.

30. A compound of the formula I as claimed in claim 27:

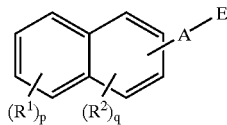

(I)

where
p is 0 to 4, q is 0 to 3;
provided when q is 0, p is 1 to 4;
—A—E is attached to the 2 position of the naphthalene ring;
—A— represents a group —$CR^5$=$CR^6$ or —COO—,
$R^5$ and $R^6$ are each independently hydrogen or $C_1$–$C_6$ alkyl, a substituted or unsubstituted phenyl, carboxy ($C_1$–$C_6$)alkyl or cyano;
E represents the group i)
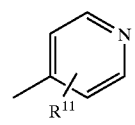
or vii)
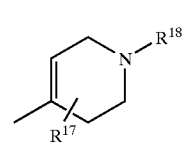

wherein
$R^{11}$, $R^{17}$ and $R^{18}$, are each independently selected from C1–C6 alkyl, C1–C6 alkoxy, halogen, trifluoromethyl, amino, a substituted or unsubstituted phenyl, and a substituted or unsubstituted phenoxy;
$R^1$ and $R^2$ are each independently selected from $C_1$–$C_6$ alkyl, hydroxy, $C_1$–$C_6$ alkoxy, nitro, cyano, $C_1$–$C_6$ alkylthio, halogen, trifluoromethyl, a substituted or unsubstituted phenyl, a substituted or unsubstituted benzyl or a group represented by —O—$(CH_2)_{m'}$—Y, in which Y represents $C_3$–$C_6$ cycloalkyl, $C_2$–$C_6$ alkenyl, $C_2$–$C_6$ alkynyl, a substituted or unsubstituted phenyl, $C_1$–$C_6$ alkoxy, and m' is 0 or 1;

or a pharmaceutically acceptable salt or ester thereof, provided that when m' represents 0, Y does not represent $C_1$–$C_6$ alkoxy.

31. A compound of formula I selected from the group consisting of

4-[2-(2-(1-methoxy)naphthyl)vinyl]pyridine,
4-[2-(2-(1-ethoxy)naphthyl)vinyl]pyridine,
4-[2-(2-(1-propyloxy)naphthyl)vinyl]pyridine hydrochloride,
4-[2-(2-(1-ethoxycarbonylmethyl)oxy)naphthyl)vinyl] pyridine,
4-[2-(2-(1-(methoxyethoxy)naphthyl)vinyl]pyridine hydrochloride,
4-[2-(2-(1-(cyclopropylmethyloxy)naphthyl)vinyl]pyridine hydrochloride,
4-[2-(2-(1-propargyloxy)naphthyl)vinyl]pyridine, 4-[2-(2-(1-bromo)naphthyl)vinyl]pyridine,
4-[2-(2-(1-(thiomethyl)naphthyl)vinyl]pyridine,
4-[2-(2-(1-chloro)naphthyl)vinyl]pyridine,
4-[2-(2-(1-cyano)naphthyl)vinyl]pyridine,
4-[2-(2-(1-trifluoromethyl)naphthyl)vinyl]pyridine,
4-[2-(2-(1-nitro)naphthyl)vinyl]pyridine,
4-[2-(2-(3-(methyl)naphthyl)vinyl]pyridine,
4-[2-(2-(3-(chloro)naphthyl)vinyl]pyridine,
4-[2-(2-(3-(thiomethyl)naphthyl)vinyl]pyridine,
trans-3-fluoro-4-[2-(2-naphthyl)vinyl]pyridine,
cis-3-fluoro-4-[2-(2-naphthyl)vinyl]pyridine, and
4'-pyridyl 1-methoxy-2-naphthoate.

* * * * *

UNITED STATES PATENT AND TRADEMARK OFFICE
CERTIFICATE OF CORRECTION

PATENT NO. : 6,846,830 B2
DATED : January 25, 2005
INVENTOR(S) : Baker et al.

It is certified that error appears in the above-identified patent and that said Letters Patent is hereby corrected as shown below:

Column 35,
Line 24, reads "...$C_3$-$C_6$ alkoxy, and", should read -- ...$C_1$-$C_6$ alkoxy, and --
Line 26, reads "...Y represents $C_1$-$C_6$...", should read -- ...Y represents $C_3$-$C_6$... --

Signed and Sealed this

Tenth Day of May, 2005

JON W. DUDAS
*Director of the United States Patent and Trademark Office*